United States Patent [19]

Lineback

[11] Patent Number: 4,936,315

[45] Date of Patent: Jun. 26, 1990

[54] METHODS AND APPARATUS FOR OBTAINING ARTERIAL BLOOD SAMPLES

[76] Inventor: Paul I. Lineback, 3071 Meder Rd., Cameron Park, Calif. 95682

[21] Appl. No.: 260,195

[22] Filed: Oct. 20, 1988

[51] Int. Cl.$^5$ .............................................. A61B 5/00
[52] U.S. Cl. ..................................... 128/765; 604/187
[58] Field of Search ....................... 128/763, 765, 770; 604/51, 52, 190, 191, 222, 231, 264, 272, 411, 412, 53, 187

[56] References Cited

U.S. PATENT DOCUMENTS

| | | | |
|---|---|---|---|
| 3,660,037 | 5/1972 | Sokol | 128/765 |
| 3,943,917 | 3/1976 | Johansen | 128/763 |
| 4,041,934 | 8/1977 | Genese | 128/763 |
| 4,159,713 | 7/1979 | Prais | 128/765 |
| 4,206,768 | 6/1980 | Bailey | 128/763 |
| 4,212,307 | 7/1980 | Raitto | 128/763 |
| 4,327,745 | 5/1982 | Ford, Jr. | 128/765 |
| 4,340,067 | 7/1982 | Rattenborg | 128/763 |
| 4,361,155 | 11/1982 | Anastasio | 128/763 |
| 4,560,378 | 12/1985 | Weiland | 604/187 |
| 4,643,200 | 2/1987 | Jennings | 128/763 |
| 4,660,569 | 4/1987 | Etherington | 128/765 |
| 4,774,963 | 10/1988 | Ichikawa et al. | 128/763 |

Primary Examiner—Max Hindenburg
Attorney, Agent, or Firm—Workman, Nydegger & Jensen

[57] ABSTRACT

Apparatus and methods for simultaneously obtaining clinical laboratory and arterial blood gas samples are disclosed. The apparatus includes a flow-through plunger configured for being detachably secured to the tip of a standard arterial blood gas syringe. The flow-through plunger has a conduit through the center thereof which permits blood to flow through the plunger into the arterial blood gas syringe. The flow-through plunger preferably has a diameter larger than the diameter of the arterial blood gas syringe. In this way, the combination of flow-through plunger and arterial blood gas syringe function as a plunger assembly for a larger syringe, preferably a clinical laboratory blood sample syringe.

Both a clinical laboratory blood sample and an arterial blood gas sample may be obtained by introducing arterial blood into the clinical laboratory syringe barrel and passing the blood through the flow-through plunger into the arterial blood gas syringe. Arterial blood may be introduced into the clinical laboratory syringe through either a direct hypodermic needle puncture into an artery or by coupling the laboratory syringe barrel to an ex-vivo arterial blood source.

24 Claims, 1 Drawing Sheet

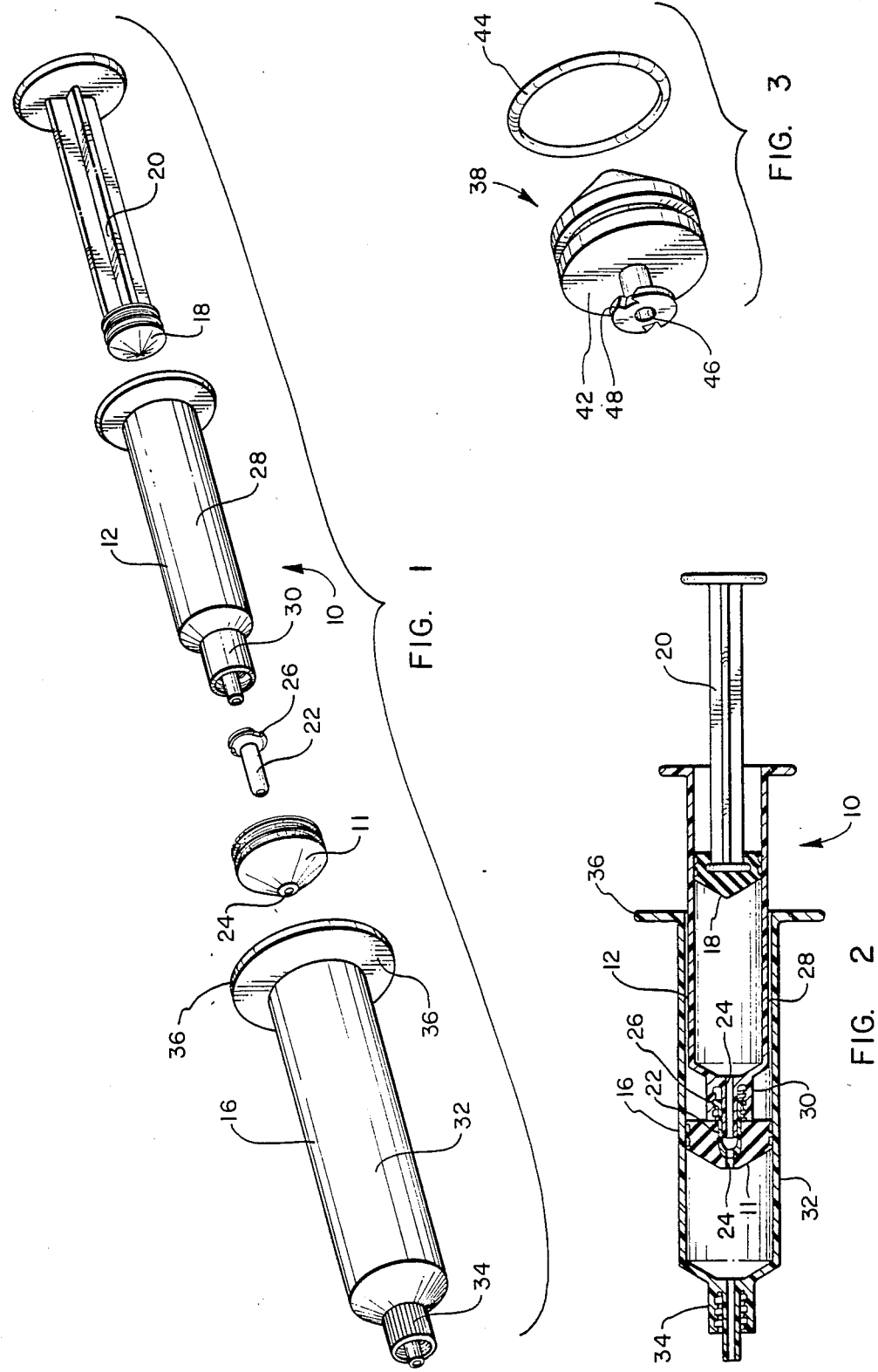

METHODS AND APPARATUS FOR OBTAINING ARTERIAL BLOOD SAMPLES

BACKGROUND OF THE INVENTION

1. Field of the Invention

The invention relates to apparatus and methods for obtaining blood samples. More particularly, the present invention is directed to apparatus and methods for obtaining both arterial blood gas and clinical laboratory samples from a single hypodermic needle puncture of a patient.

2. Technology Review

Blood samples are routinely obtained in virtually all areas of medical health care. Analysis of a person's blood provides a significant amount of information regarding the person's overall state of health. Blood for clinical laboratory analysis is most often obtained by venipuncture (puncture of a vein). Puncturing a vein to obtain blood for clinical laboratory analysis is preferred in most cases because veins are generally close to the skin's surface, transport large quantities of blood, and the blood flows in the vein at a lower pressure than in the arteries.

In specific instances, however, venous blood samples do not provide the information desired. Many times it is necessary to know the arterial blood gas concentration and pH of the arterial blood in order to correctly diagnose and treat certain diseases and conditions. Arterial blood gas (sometimes referred to as "ABG") analysis provides a measurement of the partial pressure of oxygen and of carbon dioxide in arterial blood, as well as the pH of the blood. The partial pressure of oxygen, together with hemoglobin (hemoglobin is also derived from an ABG), is a measurement of the amount of oxygen in arterial blood. Arterial blood gas analysis provides means for assessing the adequacy of oxygenation and ventilation of the blood. This provides a direct indication of lung function in supplying oxygen to the body and in removing carbon dioxide. Arterial blood gas analysis also provides information regarding the acid-base balance in the body and whether acidosis or alkalosis is present and if so to what degree.

Obtaining a sample of arterial blood for blood gas analysis is generally much more difficult than obtaining a sample of blood from a vein. Arteries are generally located deeper within the patient making them more difficult to locate and requiring a deeper hypodermic puncture. Arteries also operate under significantly higher pressure than veins, increasing the risk of hemorrhage after puncturing the artery. Perhaps the most significant procedural difference in obtaining arterial samples as opposed to venous samples is that the arterial blood samples are preferably not exposed to air. Any air bubbles in the arterial blood sample may affect the ultimate measurement of the partial pressure of oxygen within the blood.

Increasingly the blood gas technician is being asked to collect not only a sample for blood gas analysis, but also a sample for standard clinical laboratory analysis. Normally the two blood samples are obtained by independently puncturing a vein to obtain the clinical laboratory blood sample and puncturing an artery to obtain the arterial blood gas sample. This technique, however, requires two separate needle punctures to obtain the two blood samples. This technique increases the time and difficulty in obtaining the necessary samples.

In some situations it may be difficult or inconvenient for the technician to obtain blood from a vein, yet both a clinical laboratory sample and an arterial blood gas sample are needed. Such cases may arise, for example, in a code blue emergency situation (cardiac arrest) or where a suitable vein cannot be located on the patient. In these cases, one technique for obtaining both clinical laboratory blood samples and arterial blood gas samples is by taking a blood gas syringe with a three-way valve stop-cock placed between the blood gas syringe tip and the hypodermic needle. The clinical laboratory blood sample syringe is attached to the three-way valve at a right angle to the blood gas syringe. Using this apparatus, the three-way valve is positioned such that the blood gas syringe fills. Then the valve is turned, while the needle is still placed within the artery, such that the laboratory sample syringe is filled. This apparatus permits both blood samples to be obtained from a single arterial puncture.

This technique, however, requires two technicians. The first technician punctures the artery and obtains the arterial blood gas sample. Once the blood gas sample is obtained, the second technician must turn the three-way valve to direct the blood flow into the clinical laboratory syringe and the pull on the clinical laboratory syringe plunger to fill the syringe with blood. This "pulling" is at a 90° angle from the blood gas syringe while the needle is within the artery. The first technician must hold the hypodermic needle within the artery steady while the second technician draws the clinical laboratory blood sample.

This procedure is both inefficient and awkward for the technicians. Moreover, the method poses the clear danger of trauma to the artery. It is generally recognized that when manual withdrawal of the blood gas syringe piston is required, traumatization of the artery may result. The risk of trauma is particularly severe where the clinical laboratory piston is pulled at a 90° angle relative to the needle within the artery. There is a significant risk that the sharp tip of the hypodermic needle could sever or damage the artery resulting in serious hemorrhage.

An arterial line catheter is often inserted into patients from whom frequent arterial blood samples are required. The arterial line catheter is kept free of blood clots by the pressurized flow of an anticoagulant, such as sodium heparin, through the catheter. In order to obtain an arterial blood sample from an arterial line, a stop-cock in the arterial line catheter is adjusted to stop the anticoagulant flow and permit the arterial blood to fill the line. The desired samples are then taken. For each sample, the arterial line is momentarily open and exposed to the atmosphere. Thus, where both a clinical laboratory sample and blood gas sample are requested, the arterial line is open at least three times: first, to connect an arterial blood gas syringe; second, to remove the arterial blood gas syringe and connect the clinical laboratory syringe; and third, to remove the clinical laboratory syringe. Each time the arterial line is open, there is a risk of introducing infection into the patient.

From the foregoing, it will be appreciated that what is needed in the art are apparatus and methods for obtaining clinical laboratory and arterial blood gas samples which require only a single hypodermic needle puncture. It would be a significant advancement in the art to provide apparatus and methods for obtaining clinical laboratory and arterial blood gas samples which reduce the risk of arterial trauma to the patient.

It would be a further advancement in the art to provide apparatus and methods for obtaining clinical laboratory and arterial blood gas samples in which only one technician is required to obtain both samples. It would be yet another important advancement in the art to provide apparatus and methods for obtaining clinical laboratory and arterial blood gas samples which reduce the risk of infection to the patient.

Such methods and apparatus are disclosed and claimed herein.

BRIEF SUMMARY AND OBJECTS OF THE INVENTION

The present invention is directed to a dual-chambered linear syringe. The invention can be used anytime it is necessary to obtain two independent fluid samples from a single source. For example, the present invention may be used for obtaining blood samples or samples of other body fluids. The present invention may even by adapted for non-medical uses.

Preferably, the present invention includes a proximal syringe (proximal to the technician) nested within a larger distal syringe barrel. An important feature of the present invention is a flow-through plunger configured for being detachably secured to the tip of the proximal syringe. The flow-through plunger is attached to the proximal syringe in the same manner as a hypodermic needle is attached to the syringe, such as through a luer lock-type coupling. The flow-through plunger has a conduit through the center thereof which permits the fluid sample to flow from the larger distal syringe, through the plunger, and into the proximal syringe.

The flow-through plunger preferably has a diameter slightly larger than the diameter of the proximal syringe. The flow-through plunger includes a piston having sealing means radially disposed about the outer periphery of the piston for forming a slidable seal within the distal syringe barrel. In this way the flow-through plunger, in combination with the proximal syringe, function as a plunger assembly for the distal syringe.

In one preferred embodiment within the scope of the present invention, the proximal syringe comprises a standard arterial blood gas syringe, and the distal syringe comprises a clinical laboratory syringe. This embodiment is configured for obtaining both a clinical laboratory blood sample and an arterial blood gas sample from a single source of arterial blood.

As discussed above, the apparatus of the present invention may be used to obtain two fluid samples from a single fluid source. One method for obtaining such fluid samples includes connecting the distal syringe of the fluid source. This may involve the use of a hypodermic needle if a body fluid is to be obtained, or the use of some other connecting means. The fluid samples are then obtained by drawing the proximal syringe out of the distal syringe barrel, thereby filling the distal syringe barrel with one fluid sample. The plunger shaft within the proximal syringe is then preferably withdrawn to obtain the fluid sample within the proximal syringe barrel. It will be appreciated that the fluid sample flows from the distal syringe barrel, through the flow-through plunger, and into the proximal syringe.

The method for obtaining a clinical laboratory blood sample and arterial blood gas sample from a single hypodermic needle puncture varies depending upon the source of arterial blood. For example, if the blood is to be obtained directly from a patient's artery, the arterial blood gas syringe preferably has a vented plunger within the syringe barrel or a plunger having a gas permeable, but liquid impermeable, membrane. Plungers which allow the air within the syringe to escape as the syringe fills with blood are referred to generically as vented plungers.

Prior to inserting the hypodermic needle into the artery, the vented plunger and the flow-through plunger are preferably adjusted within their respective syringe barrels to a preset location representing the desired quantity of blood for both blood samples. Upon puncturing the artery, both syringe barrels rapidly fill with blood from the arterial blood pressure. As the blood fills the syringe barrels, the air within the syringe barrels is vented through the vented plunger. In this way, air bubbles introduced into the arterial blood gas sample are minimized.

If the source of arterial blood is from an arterial line catheter, or an umbilical arterial catheter, then the plunger within the arterial blood gas syringe does not need to be vented. An air-tight unit may be preferred.

Both the flow-through syringe plunger and the plunger within the arterial blood gas syringe are preferably positioned far into their respective syringe barrels. By pulling back on the proximal blood gas syringe, which is attached to the flow-through plunger, the distal clinical laboratory syringe is filled with blood. The proximal blood gas syringe plunger is then pulled back to obtain the arterial blood gas sample. The blood flows from the distal clinical laboratory syringe barrel through the flow-through plunger, and into the proximal arterial blood gas syringe barrel.

In both of the foregoing methods, the proximal blood gas syringe may contain a quantity of anticoagulant to inhibit coagulation of the blood sample. An anticoagulant is desired because the coagulation process alters the true blood gas values. Moreover, it would be difficult or impossible to accurately measure blood gas values from a coagulated mass of blood.

After both blood samples are obtained, the proximal blood gas syringe is removed from the flow-through plunger and capped. The distal clinical laboratory syringe is capped at the plunger site by replacing the arterial blood gas syringe with a conventional plunger rod adapted to twist onto the flow-through plunger.

A primary object of the present invention is to provide apparatus and methods for obtaining two separate and independent fluid samples from a single fluid source.

More particularly, an object of the present invention is to provide apparatus and methods for obtaining clinical laboratory and arterial blood gas samples which require a single hypodermic needle puncture.

Another important object of the present invention is to provide apparatus and methods for obtaining clinical laboratory and arterial blood gas samples which reduce the risk of trauma to the patient.

An additional object of the present invention is to provide apparatus and methods for obtaining clinical laboratory and arterial blood gas samples in which only one technician is required to obtain both samples.

A further object of the present invention is to provide apparatus and methods for obtaining clinical laboratory and arterial blood gas samples which reduce the risk of infection to the patient.

These and other objects and features of the present invention will become more fully apparent from the following description and appended claims taken in conjunction with the accompanying drawings, or may be learned from the practice of the invention.

BRIEF DESCRIPTION OF THE DRAWINGS

FIG. 1 is an exploded perspective view of one embodiment of a dual-chambered linear syringe structure within the scope of the present invention;

FIG. 2 is an assembled longitudinal cross-sectional view of the embodiment illustrated in FIG. 1; and FIG. 3 is a perspective view of a flow-through plunger within the scope of the present invention.

DETAILED DESCRIPTION OF THE PREFERRED EMBODIMENTS

Reference is now made to the drawings wherein like parts are designated with like numerals throughout. Referring first to FIG. 1, one presently preferred embodiment of the apparatus of the present invention is illustrated in an exploded perspective format. The present invention is a dual-chambered linear syringe 10 designed for obtaining two separate and independent fluid samples from a single fluid source.

The two chamber are formed by a smaller, proximal syringe 12 positioned within a larger, distal syringe 16. The conventional plunger and plunger shaft normally associated with the distal syringe are replaced by a flow-through plunger 11 attached to the tip of the proximal syringe 12. Thus, the flow-through plunger 11 and the proximal syringe 12 combine to act as a plunger and plunger shaft for the distal syringe 16. The proximal syringe 12 includes a conventional plunger 18 and plunger shaft 20.

In operation, the flow-through plunger 11 and proximal syringe 12 provide a piston function for the distal syringe 16, permitting the distal syringe 16 to be filled with the desired fluid sample. Similarly, actuating the conventional plunger 18 and plunger shaft 20 within the proximal syringe 12 permits the proximal syringe 12 to be filled with the fluid sample. The fluid sample flows from the distal syringe 16 to the proximal syringe 12 by passing through the flow-through plunger 11.

FIG. 1 shows one embodiment of the flow-through plunger 11, a proximal syringe 12, and a distal syringe 16. Flow-through plunger 11 includes a flow-through adapter 22. Plunger 11 is constructed much like conventional syringe plungers except that plunger 11 includes a conduit 24 or bore through the center thereof to allow the passage of blood or other fluids through the piston. Plunger 11 is preferably constructed of a hard compressed rubber or other suitable resilient material which is capable of forming a slidable seal within a distal syringe 16.

Flow-through adapter 22 is designed to be attached to plunger 11 such that the flow-through adapter and piston together form conduit 24. Flow-through adapter 22 is preferably press fit and sealed within conduit 24 and held in place due to pressure and sealant from the resilient material of plunger 11. Flow-through adapter 22 is generally tubular in shape such that when positioned within plunger 11, conduit 24 continues through flow-through adapter 22 creating an open passageway through the center of the flow-through plunger 11.

Flow-through adapter 22 may have a twisting lip 26 adapted to be removable secured to a twist-on locking device or luer lock-type coupling mechanism found on many conventional syringe tips. In one preferred embodiment, twisting lip 26 is a male luer lock coupling.

Because flow-through adapter 22 is adapted to be removably secured to the syringe tips, flow-through adapter 22 is preferably constructed of a rigid material. It has been found that existing hard plastic materials used in the medical arts are suitable materials.

Proximal syringe 12 includes a syringe barrel 28 and a plunger shaft 20. Proximal syringe 12 is preferably a conventional arterial blood gas syringe. Plunger shaft 20 is preferably positioned within proximal syringe barrel 12. At the distal end of plunger shaft 20 is a plunger 18. Plunger 18 is preferably a vented plunger. For the purposes of this application, a vented plunger is gas permeable but liquid impermeable. This includes both vented plungers known in the art, as well as membrane plungers such as the one described in U.S. Pat. No. 4,327,745 to Ford, issued May 4, 1982.

At the distal end of proximal syringe barrel 28 is coupling device 30. Coupling device 30, as found on many conventional syringes, is a twist-on locking device or luer lock-type coupling known in the art. In most cases, coupling device 30 is adapted to receive a hypodermic needle. However, in the apparatus of the present invention illustrated in FIG. 1, coupling device 30 is adapted to receive flow-through plunger 11 and locks onto flow-through adapter 22.

Also illustrated in FIG. 1 is distal syringe 16. Distal syringe 16 is preferably a conventional syringe for obtaining a clinical laboratory blood sample. Distal syringe 16 includes a distal syringe barrel 32 having a inside diameter configured to receive flow-through plunger 11. A coupling device 34 is located at the proximal end of distal syringe barrel 32. Coupling device 34 is preferably a conventional twist-on locking device or luer lock-type coupling similar to coupling device 30. Coupling device 34 is configured for receiving a hypodermic syringe needle (not shown) or the luer lock coupling of a three way stop-cock. At the proximal end of distal syringe barrel 32 is an annular lip 36.

Referring now to FIG. 2, the embodiment of FIG. 1 is assembled and illustrated in a cross-sectional view. In FIG. 2, proximal syringe 12 is shown with a smaller outside diameter than the inside diameter of distal syringe 16. In this manner, proximal syringe 12 may literally fit inside distal syringe 16.

As discussed above, proximal syringe 12 may preferably be a conventional arterial blood gas syringe and distal syringe 16 may preferably be a clinical laboratory syringe. Generally, the blood sample size required for clinical laboratory analysis is significantly larger than the sample size required for blood gas analysis. Typically, an arterial blood gas sample should be in the range from about 1 cc (cubic centimeter) to about 3 cc, whereas a typical clinical laboratory blood sample may range from about 6 cc to about 20 cc, depending on the particular set of conditions. Thus, although it would be possible to reverse the functions of the proximal and distal syringes, in most cases it is preferable to obtain a larger clinical laboratory sample than arterial blood gas sample.

The method for obtaining a clinical laboratory blood sample and arterial blood gas sample from a single hypodermic puncture varies depending upon the source of arterial blood. If the blood is to be obtained directly from a patient's artery, then plunger 18 of the proximal syringe 12 is preferably vented. A vented plunger 18 allows air within both syringes 12 and 16 to escape as the syringe fills with blood.

Prior to inserting the hypodermic needle into the artery, plunger 18 and flow-through plunger 11 are preferably adjusted within proximal syringe barrel 12 and distal syringe barrel 16, respectively, to a preset location representing the desired quantity of blood for both blood samples. Upon puncturing an artery, both syringe barrels fill with blood under the arterial blood pressure. As blood fills the syringe barrels, the air within the syringe barrels is vented through the vented plunger 18. In this manner, air bubbles within the arterial blood gas sample are minimized.

If the source of arterial blood is from an arterial line catheter, an umbilical arterial catheter, or some other external arterial blood source, then plunger 18 is not necessarily vented. As a result, proximal syringe 12 in this situation, would preferably be a conventional airtight syringe. Both flow-through syringe plunger 11 and plunger 18 are preferably positioned far into their respective syringe barrels. By pulling back on proximal syringe 12, to which the flow-through plunger 11 is attached, distal syringe barrel 32 is filled with blood. Plunger shaft 20 is then preferably pulled back to obtain the arterial blood gas sample within proximal syringe barrel 12. The blood flows from distal syringe barrel 32 through flow-through plunger 11, and into proximal syringe barrel 12.

In both of the foregoing methods, proximal syringe barrel 12 preferably contains a quantity of anticoagulant to inhibit coagulation of the blood gas sample. An anticoagulant is desired because blood coagulation destroys the integrity of accurate blood gas analysis. Any suitable anticoagulant known in the art may be used. It has been found that lithium heparin produces satisfactory results.

After both blood samples are obtained, the proximal syringe 12 is removed from the flow-through plunger 11 by simply untwisting coupling device 30. Any incidental air bubbles remaining within proximal syringe barrel 12 are removed and coupling device 30 is capped to prevent atmospheric gas from compromising the blood gas analysis. The distal syringe, containing the clinical laboratory blood sample, is then capped at the flow-through plunger site by replacing proximal syringe 12 with a conventional plunger shaft or other type of plug (not shown) adapted to twist onto the flow-through syringe plunger 11. The blood samples are then delivered to their respective laboratories for analysis.

FIG. 3 illustrates an additional embodiment of a flow-through plunger assembly 38 within the scope of the present invention. Flow-through assembly 38, shown in an exploded format, includes a flow-through plunger 42 and an O-ring 44. Flow-through plunger 42 has a conduit 46 or bore through the center thereof to permit blood or fluid to flow through the flow-through plunger 42. A twisting lip 48 is secured to flow through plunger 42. In one preferred embodiment within the scope of the present invention, twisting lip 48 is integrally molded with flow-through plunger 42. Twisting lip 48 is adapted to be removably secured to a conventional twist-on locking device or luer lock-type coupling.

When assembled O-ring 44 is radially disposed about the outer periphery of flow-through plunger 42. O-ring 44 provides means for forming a slidable seal within a distal syringe barrel. O-ring 44 is preferably constructed of a resilient material such as hard compressed rubber.

In summary, the present invention provides apparatus and methods for obtaining two independent fluid samples from a single fluid source. More particularly, the present invention provides apparatus and methods for obtaining clinical laboratory and arterial blood gas samples which require only a single hypodermic needle puncture to a patient. This is accomplished by the unique dual-chamber linear syringe disclosed herein which features a flow-through plunger.

The present invention further provides apparatus and methods for obtaining clinical laboratory and arterial blood gas samples which reduce the risk of trauma to the patient's arteries. Only a single puncture is required and no twisting of the device is required while the needle is disposed within the artery. In addition, only one technician is required to obtain both blood samples instead of two technicians required for existing techniques.

Furthermore, because the present invention enables both the clinical laboratory and arterial blood gas samples to be obtained simultaneously, the risk of infection to the patient is substantially reduced. No manipulations are required that would expose a patient's artery to an unsterile outside environment.

The invention may be embodied in other specific forms without departing from its spirit or essential characteristics. The described embodiments are to be considered in all respects only as illlustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dual-chambered linear syringe for simultaneously obtaining two fluid samples from a single fluid source comprising:
    a distal syringe barrel having a first open end, a second open end adapted for attachment to a fluid source, and a bore communicating between said ends;
    a proximal syringe barrel having a first open end, a second open end, and a bore communicating between said ends, said proximal syringe barrel having an outside diameter smaller than the inside diameter of the distal syringe barrel;
    a flow-through plunger detachably secured to the second open end of the proximal syringe and configured such that it is capable of forming a slidable seal within the bore of said distal syringe barrel, said flow-through plunger having a conduit through the center thereof to permit fluid flow therethrough;
    wherein said proximal and distal syringe barrels are detachable in such a manner as to leave said flow-through plunger within said distal syringe barrel such that two generally enclosed fluid samples can be simultaneously obtained from a single fluid source in communication with said distal syringe.

2. A dual-chambered linear syringe for simultaneously obtaining two fluid samples from a single fluid source as defined in claim 1, wherein the proximal syringe barrel comprises an arterial blood gas syringe.

3. A dual-chambered linear syringe for simultaneously obtaining two fluid samples from a single fluid source as defined in claim 1, wherein the proximal syringe barrel has a volume for obtaining a blood sample size in the range from about 1 cc to about 2 cc.

4. A dual-chambered linear syringe for simultaneously obtaining two fluid samples from a single fluid source as defined in claim 2, wherein the arterial blood gas syringe further comprises a slidable plunger which is gas permeable and liquid impermeable.

5. A dual-chambered linear syringe for simultaneously obtaining two fluid samples from a single fluid source as defined in claim 1, wherein the flow-through plunger is detachably secured to the second open end of the proximal syringe barrel through use of a luer lock coupling.

6. A dual-chambered linear syringe for simultaneously obtaining two fluid samples from a single fluid source as defined in claim 1, wherein the sealing means comprises an O-ring disposed around the outside diameter of the flow-through plunger.

7. A dual-chambered linear syringe for simultaneously obtaining two fluid samples from a single fluid source as defined in claim 1, wherein the flow-through plunger and the sealing means are integrally molded.

8. A syringe for simultaneously obtaining two liquid samples from a single source comprising:
   a distal syringe comprising a distal syringe barrel having a first open end, a second open end adapted for mounting a detachable hypodermic needle on the opening thereof, and a bore communicating between said ends;
   a generally cylindrical plunger slidably mounted within the bore of the distal syringe barrel having a distal end, a proximal end, and conduit means through the center thereof to permit the flow of liquid therethrough;
   sealing means radially disposed about the outer periphery of said plunger for forming a slidable seal within the bore of said distal syringe barrel;
   a proximal syringe comprising a proximal syringe barrel having a first open end for receiving a slidable plunger, a second open end adapted for receiving the cylindrical plunger on the opening thereof, and a bore communicating between said ends;
   means for detachably securing the cylindrical plunger to the second open end of the proximal syringe barrel such that when the cylindrical piston is secured to the proximal syringe barrel and positioned within the distal syringe barrel, the conduit means of the cylindrical piston provides a fluid passageway from the distal syringe barrel to the proximal syringe barrel and such that the proximal syringe can be detached leaving the plunger within the distal syringe; and
   a plunger slidably mounted in the bore of the proximal syringe barrel having a plunger shaft partially extending out of the first open end of the proximal syringe barrel.

9. A syringe device for obtaining a clinical laboratory blood sample and an arterial blood gas sample from a patient as defined in claim 8, wherein the proximal syringe comprises an arterial blood gas syringe.

10. A syringe device for obtaining a clinical laboratory blood sample and an arterial blood gas sample from a patient as defined in claim 9, wherein the proximal syringe is configured to obtain a blood sample size in the range from about 1 cc to about 3 cc.

11. A syringe device for obtaining a clinical laboratory blood sample and an arterial blood gas sample from a patient as defined in claim 10, wherein the proximal syringe includes a slidable plunger which is gas permeable and liquid impermeable.

12. A syringe device for obtaining a clinical laboratory blood sample and an arterial blood gas sample from a patient as defined in claim 10, wherein the distal syringe comprises a clinical laboratory syringe.

13. A syringe device for obtaining a clinical laboratory blood sample and an arterial blood gas sample from a patient as defined in claim 12, wherein the distal syringe is configured to obtain a blood sample size in the range from about 6 cc to about 20 cc.

14. A syringe device for obtaining a clinical laboratory blood sample and an arterial blood gas sample from a patient as defined in claim 13, wherein the means for detachably securing the cylindrical plunger to the second open end of the proximal syringe barrel comprises a male luer lock coupling.

15. A syringe device for obtaining a clinical laboratory blood sample and an arterial blood gas sample from a patient as defined in claim 14, wherein the cylindrical plunger and the male luer lock coupling are integrally molded.

16. A syringe device for obtaining a clinical laboratory blood sample and an arterial blood gas sample from a patient as defined in claim 15, wherein the sealing means comprises an O-ring.

17. A syringe device for obtaining a clinical laboratory blood sample and an arterial blood gas sample from a patient as defined in claim 14, wherein the plunger and the sealing means are integrally molded of a resilient material.

18. A method for simultaneously obtaining two fluid samples from a single fluid source comprising the steps of:
   obtaining a dual-chambered linear syringe comprising a distal syringe, a proximal syringe positioned within the distal syringe, and a flow-through plunger detachably secured to the proximal syringe and positioned within the distal syringe, said flow-through plunger comprising conduit means through the center thereof to permit fluid flow from the distal syringe into the proximal syringe and sealing means radially disposed about the outer periphery of said flow-through syringe plunger for forming a slidable seal within the distal syringe, said flow-through plunger, said plunger being detachable from said proximal syringe in such a manner as to leave the plunger within the distal syringe;
   connecting the distal syringe with a fluid source;
   introducing fluid into the distal syringe; and
   passing at least a portion of the fluid through the flow-through plunger into the proximal syringe.

19. A method for simultaneously obtaining two fluid samples from a single fluid source as defined in claim 18, wherein the fluid to be sampled comprises blood.

20. A method for simultaneously obtaining two fluid samples from a single fluid source as defined in claim 18 wherein the connecting step comprises attaching a hypodermic needle to a syringe tip formed on the distal syringe and inserting the hypodermic needle into an artery of a patient.

21. A method for simultaneously obtaining two fluid samples from a single fluid source as defined in claim 18 wherein the connecting step comprises removably attaching the distal syringe to an arterial line catheter, or umbilical arterial catheter.

22. A method for simultaneously obtaining two fluid samples from a single fluid source as defined in claim 21, wherein the introducing step comprises telescopically withdrawing the plunger/syringe assembly from within the distal syringe, thereby filling the distal syringe with blood.

23. A method for simultaneously obtaining two fluid samples from a single fluid source as defined in claim 22, wherein the passing step comprises telescopically withdrawing a slidable plunger positioned within the proximal syringe, thereby causing blood to pass through the flow-through plunger and fill the proximal syringe with blood.

24. A method for simultaneously obtaining a clinical laboratory blood sample and an arterial blood gas sample from a single hypodermic needle puncture comprising the steps of:

obtaining a dual-chambered linear syringe having a clinical laboratory syringe, an arterial blood gas syringe having a vented plunger therewithin, and a flow-through plunger detachable secured to a syringe tip formed on the arterial blood gas syringe, said flow-through plunger comprising conduit means through the center thereof to permit blood flow into the arterial blood gas syringe and sealing means radially disposed about the outer periphery of said flow-through plunger for forming a slidable seal within the clinical laboratory syringe, said arterial blood gas syringe being positioned within the clinical laboratory syringe;

attaching a hypodermic needle to a syringe tip formed on the clinical laboratory syringe;

inserting the hypodermic needle into an artery thereby allowing arterial blood to flow into the clinical laboratory syringe, through the flow-through syringe plunger, and into the arterial blood gas syringe;

removing the hypodermic needle from the artery; and separating the arterial blood gas syringe from the flow-through plunger within the flow-through syringe plunger remains within the clinical laboratory syringe.

* * * * *